United States Patent
Taya

(10) Patent No.: US 12,383,370 B2
(45) Date of Patent: Aug. 12, 2025

(54) MEDICAL CONTROL APPARATUS, MEDICAL SYSTEM, AND METHOD FOR CONTROLLING MARKING DEVICE

(71) Applicant: OLYMPUS CORPORATION, Tokyo (JP)

(72) Inventor: Naoya Taya, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1198 days.

(21) Appl. No.: 17/190,593

(22) Filed: Mar. 3, 2021

(65) Prior Publication Data

US 2021/0186650 A1 Jun. 24, 2021

Related U.S. Application Data

(63) Continuation of application No. PCT/JP2019/036126, filed on Sep. 13, 2019.

(60) Provisional application No. 62/731,135, filed on Sep. 14, 2018.

(51) Int. Cl.
*A61B 90/00* (2016.01)
*A61B 18/00* (2006.01)
*A61B 18/14* (2006.01)

(52) U.S. Cl.
CPC .......... *A61B 90/39* (2016.02); *A61B 18/1482* (2013.01); *A61B 2018/00982* (2013.01); *A61B 2090/3945* (2016.02)

(58) Field of Classification Search
CPC ... A61B 34/10; A61B 34/20; A61B 2034/107; A61B 2090/3945
See application file for complete search history.

(56) References Cited

U.S. PATENT DOCUMENTS

| | | | |
|---|---|---|---|
| 6,241,724 B1 | 6/2001 | Fleischman et al. | |
| 2006/0089624 A1* | 4/2006 | Voegele | A61B 34/20 606/1 |
| 2014/0371527 A1 | 12/2014 | Sato | |
| 2018/0217734 A1* | 8/2018 | Koenig | G06T 7/0012 |
| 2018/0310987 A1* | 11/2018 | Altmann | G16H 40/63 |

FOREIGN PATENT DOCUMENTS

| | | |
|---|---|---|
| JP | 2004-351230 A1 | 12/2004 |
| JP | 2007-152139 A | 6/2007 |
| JP | 2015-000093 A | 1/2015 |

(Continued)

OTHER PUBLICATIONS

International Search Report dated Oct. 29, 2019 issued in PCT/JP2019/036126.

*Primary Examiner* — Ronald Hupczey, Jr.
(74) *Attorney, Agent, or Firm* — Scully, Scott, Murphy & Presser, P.C.

(57) ABSTRACT

A medical system includes a marking device inserted into a body cavity, the marking device having an applicator configured to transmit energy so as to perform marking on target tissues; and a controller comprises at least a processor and configured to control the marking device, wherein the applicator has a plurality of application elements which individually applies energy; and wherein the controller is configured to set a marking region on the target tissues in the body cavity; and selectively control the application elements among the plurality of application elements corresponding to the marking region to apply the energy.

20 Claims, 9 Drawing Sheets

(56) References Cited

FOREIGN PATENT DOCUMENTS

| | | |
|---|---|---|
| JP | 2016-043128 A | 4/2016 |
| JP | 2018-509981 A | 4/2018 |
| JP | 6461193 B2 | 1/2019 |
| WO | WO 95/10318 A1 | 4/1995 |
| WO | WO 2016/182876 A1 | 11/2016 |

* cited by examiner

MEDICAL CONTROL APPARATUS, MEDICAL SYSTEM, AND METHOD FOR CONTROLLING MARKING DEVICE

This application is a continuation application based on a PCT International Application No. PCT/JP2019/036126, filed on Sep. 13, 2019, whose priority is claimed on a U.S. provisional application No. 62/731,135, filed on Sep. 14, 2018. The content of both the PCT International Application and the US provisional application are incorporated herein by reference.

TECHNICAL FIELD

The present disclosure relates to a medical control apparatus configured to control a marking device to perform marking through a hole on the abdominal wall and the like, a medical system having a marking device, a marking device, and a method for controlling a marking device.

BACKGROUND ART

Conventionally, procedures of performing treatment by inserting a treatment device and an endoscope through different holes (openings) on the abdominal wall respectively are used in a laparoscopic surgery. According to the laparoscopic surgery, the incised wound is small compared with an abdominal operation and the laparoscopic surgery is superior in the minimally invasive characteristic.

In a case of resecting living tissues in the laparoscopic surgery, marking on the surface of the living tissues is performed so as to clarify a separation line. A surgeon performs the marking using a marking device (monopolar device and the like) while confirming the affected area using a laparoscopic image. A filed of view is narrow under the laparoscopic observation. It is difficult to operate the treatment device and endoscope in a narrow space such as inside the body cavity. Accordingly, it is difficult to accurately perform marking on the surface of the living tissues under the laparoscopic observation and it is a time-consuming operation.

An ablation device disclosed in Japanese Patent Publication No. 6461193 has a cauterization portion having a plurality of electrodes arranged in a line. The ablation device is configured to suitably perform adjustment so as to cause a cauterization surface to be contact in the living tissues and then cauterizes the living tissues linearly along the cauterization surface having an elongated shape.

SUMMARY

According to an aspect of the present disclosure, a medical system includes a marking device inserted into a body cavity, the marking device having an applicator configured to transmit energy so as to perform marking on target tissues; and a controller comprises at least a processor and configured to control the marking device. The applicator has a plurality of application elements which individually applies energy. The controller is configured to set a marking region on the target tissues in the body cavity; and selectively control the application elements among the plurality of application elements corresponding to the marking region to apply the energy.

According to another aspect of the present disclosure, a medical control apparatus includes a control circuit configured to control a marking device inserted into a body cavity, wherein the marking device has an applicator configured to transmit energy so as to perform marking on target tissues, and the applicator has a plurality of application elements which individually applies energy. The control circuit is configured to set a marking region on the target tissues in the body cavity; and selectively control the application elements among the plurality of application elements corresponding to the marking region to apply the energy.

According to a further aspect of the present disclosure, a method for controlling a marking device inserted into a body cavity, wherein the marking device has an applicator configured to transmit energy so as to perform marking on target tissues, and the applicator has a plurality of application elements which individually applies energy, includes setting a marking region on the target tissues in the body cavity for performing the marking; and selectively controlling the application elements among the plurality of application elements corresponding to the marking region to apply the energy.

DESCRIPTION OF EMBODIMENT

First Embodiment

A first embodiment of the present disclosure will be described with reference from FIG. 1 to FIG. 11.

Figure 1:
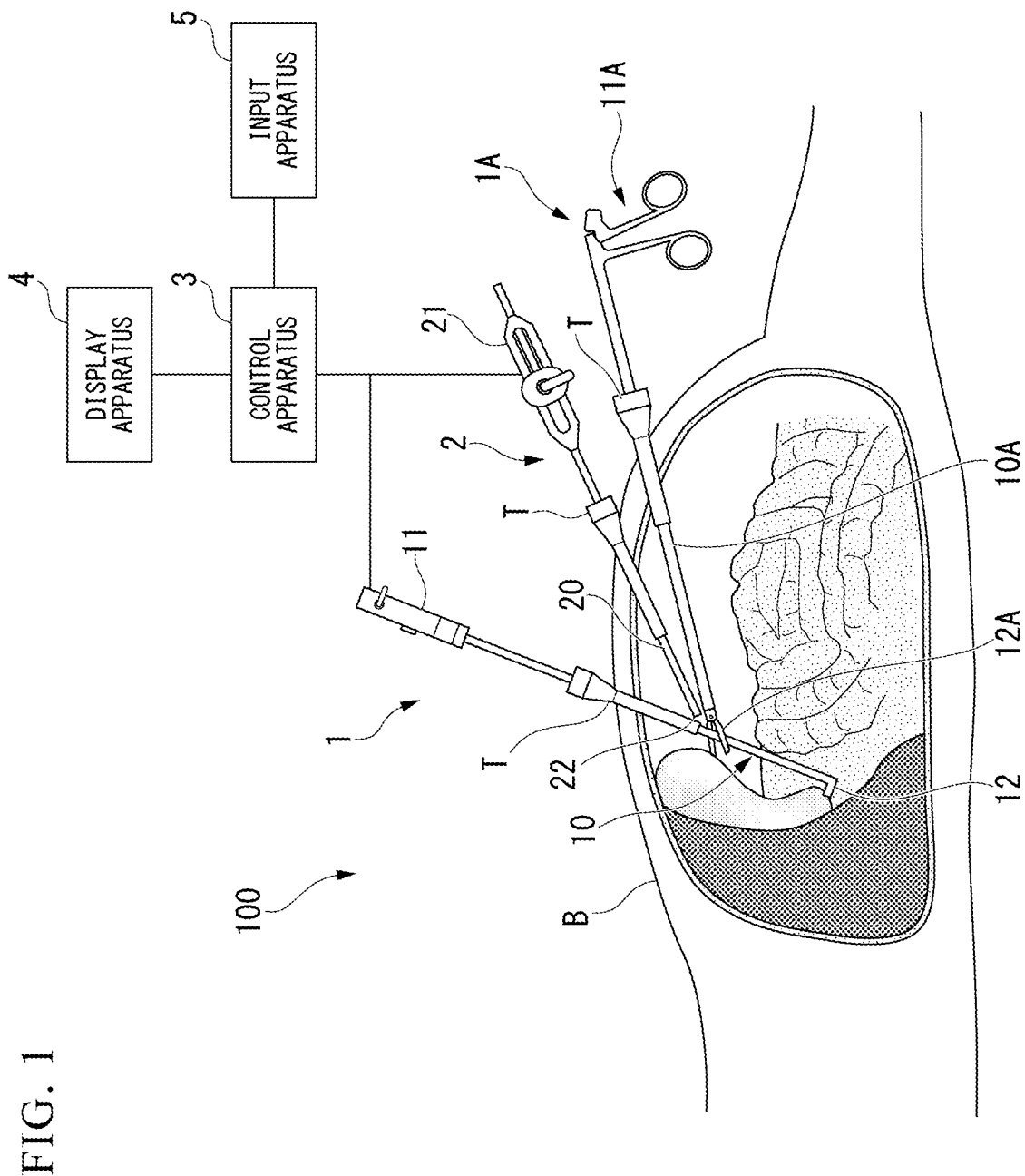
FIG. 1 is a view showing an overall configuration of a medical system having a control apparatus according to a first embodiment of the present disclosure.
Figure 2:
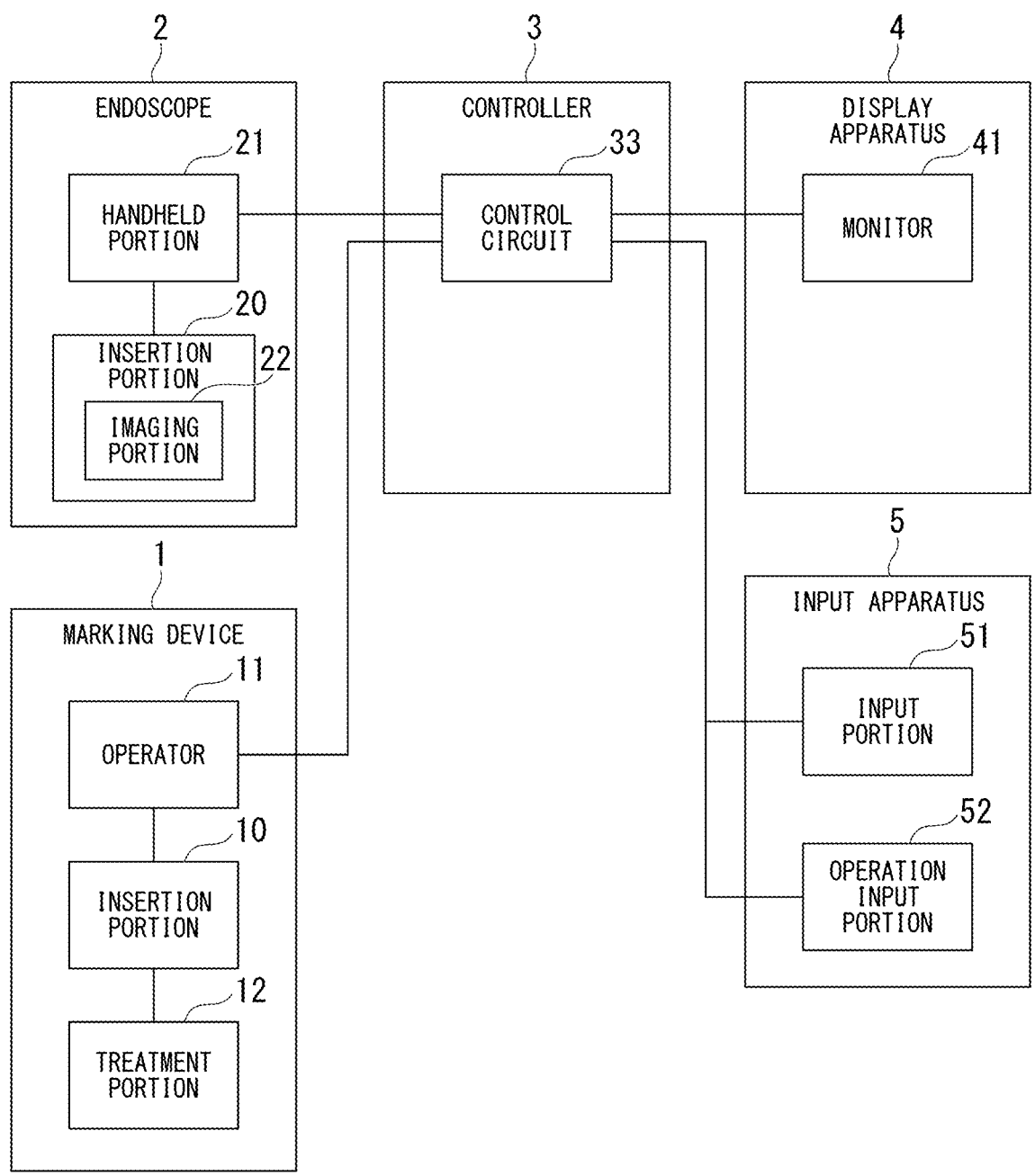
FIG. 2 is a diagram showing a hardware configuration of the medical system.

FIG. 1 is a view showing an overall configuration of a medical system 100 having a control apparatus 3 according to the present embodiment. FIG. 2 is a hardware configuration diagram of the medical system 100.

[Medical System 100]

As shown in FIG. 1 and FIG. 2, the medical system 100 has a marking device 1, an endoscope 2, a control apparatus 3, a display apparatus 4, an input apparatus 5, and an assistance treatment device 1A. The medical system 100 is configured to assist the procedures performed by inserting the marking device 1 and the endoscope 2 into the body cavity through different holes (openings) opened on the abdominal wall respectively during the laparoscopic surgery.

Figure 3:
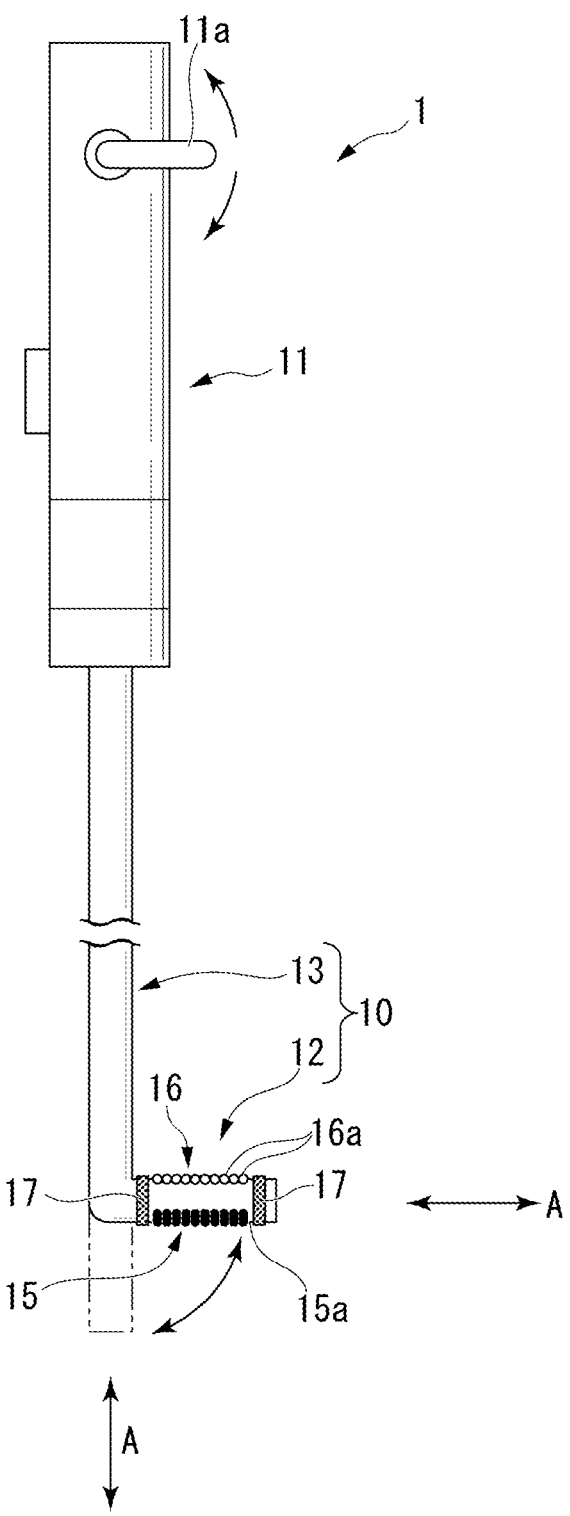
FIG. 3 is a view showing a marking device of the medical system.

FIG. 3 is a view showing the marking device 1.

The marking device (treatment device) 1 has an elongated insertion portion 10 that is insertable into the abdominal cavity (body cavity) of a patient, an operation portion 11 provided at a proximal end side of the insertion portion 10, and a treatment portion 12 provided at a distal end side of the insertion portion 10. The surgeon introduces the treatment portion 12 and the insertion portion 10 into the abdominal cavity by inserting the treatment portion 12 and the insertion portion 10 through a trocar T puncturing the abdomen B of the patient.

Figure 4:
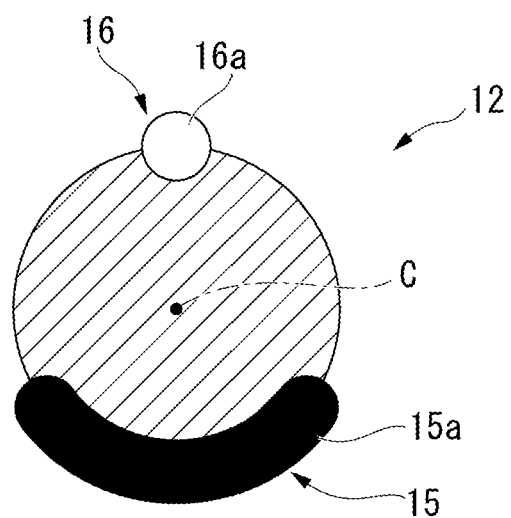
FIG. 4 is a view showing a treatment portion of the marking device when viewing from an axial direction.

FIG. 4 is a view showing the treatment portion 12 viewing from an axial direction A.

The treatment portion 12 is configured to apply a power on the affected area due to the energy supplied from an energy supply source. The treatment portion 12 is attached to the insertion portion 10 to be bendable. The treatment portion 12 is formed in a columnar shape and to be rigid. The treatment portion 12 has an applicator 15, a light emitter 16 and a marker 17. The applicator 15 and the light emitter 16 are disposed on an external circumferential surface of the treatment portion 12, while the applicator 15 and the light emitter 16 are disposed to sandwich a central axis O in the axial direction A to be at opposite sides with each other.

The applicator (energy applicator) 15 is configured to have a plurality of application elements 15a which are arrayed along the axial direction A of the treatment portion 12. According to the present embodiment, the application elements 15a are monopolar electrodes. The plurality of application elements 15a are individually controlled to generate heat. For example, there is a possibility that all of the plurality of application elements 15a are controlled to generate heat, and there is a possibility that only one selected application element 15a is controlled to generate heat. The application element 15a is formed to be elongated along a circumferential direction orthogonal to the axial direction A.

The light emitter 16 is configured to have a plurality of light-emitting elements 16a which are arrayed along the axial direction A of the treatment portion 12. The plurality of light-emitting elements 16a are individually controlled to emit light. For example, there is a possibility that all of the plurality of light-emitting elements 16a are controlled to emit light, and there is a possibility that only one selected light-emitting element 16a is controlled to emit light.

The application element 15a has a corresponding light-emitting element 16a. A pair of the application element 15a and the light-emitting element 16a are positioned at two sides of the central axis O in the axial direction A. The light-emitting element 16a is configured to emit light in response to the heat generation of the corresponding application element 15a. The surgeon can specify the heated application element 15a by visually confirming the position of the light-emitting element 16a that is emitting light.

The marker 17 is a member applied with a pattern and a color suitable for image recognition. The marker 17 is provided at two locations at the distal end side and the proximal end side in the axial direction A of the treatment portion 12. The applicator 15 and the light emitter 16 are positioned between the two markers 17.

The operation portion 11 is a member operated by the surgeon. The surgeon can change the position and orientation of the treatment portion 12 of the marking device 1 by grasping the operation portion 11 to move the marking device 1. The operation portion 11 has a handle 11a. The surgeon can bend the operation portion 12 with respect to the insertion portion 10 by rotating the handle 11a with respect to the operation portion 11.

Inside the insertion portion 10 and the operation portion 11, control-signal lines for controlling the treatment portion 12, power lines for supplying the power to the treatment portion 12 are wired therein. The control-signal lines and power lines are connected with the control apparatus 3.

As shown in FIG. 1, the assistance treatment device 1A has an elongated insertion portion 10A being insertable into the abdominal cavity of the patient and an operation portion 11A provided at a proximal end side of the insertion portion 10A. The surgeon introduces the insertion portion 10A into the abdominal cavity by inserting the insertion portion 10A through the trocar T puncturing the abdomen B of the patient.

The insertion portion 10A has a pair of grasping members 12A configured to perform treatment on the affected area of the patient at the distal end thereof. The operation portion 11A is a member configured to operate the pair of grasping members 12A. The operation portion 11A has a handle, and the operation portion 11A is configured to open and close the pair of grasping members 12A by relatively moving the handle with respect to the other part of the operation portion 11A.

The assistance treatment device 1A is introduced into the abdominal cavity so as to grasp and retain the marking device 1. The assistance treatment device 1A is not an essential configuration element of the medical system 100.

The endoscope (image apparatus) 2 has an elongated and rigid insertion portion 20 being insertable into the abdominal cavity of the patient and a handheld portion 21. The surgeon introduces the insertion portion 20 into the abdominal cavity by inserting the insertion portion 20 through the trocar T puncturing the abdomen B of the patient.

The insertion portion 20 has an imaging portion 22 at the distal end thereof. The imaging portion 22 has lens and imaging element configured to capture images inside the abdomen of the patient. The insertion portion 20 introduced into the abdominal cavity is disposed at a position so as to cause the imaging portion 22 to be able to capture images of the affected area of the treatment target inside the abdomen. The imaging portion 22 may have an optical zoom function or electrical zoom function.

The handheld portion 21 is a member operated by the surgeon. The surgeon can change the position and the orientation of the imaging portion 22 of the endoscope 2. The insertion portion 20 may further have a bending portion. It is possible to change the position and orientation of the imaging portion 22 by bending the bending portion provided in part of the insertion portion 20.

Inside the handheld portion 21, the control-signal lines for controlling the imaging portion 22, the transmission-signal lines for transmitting the captured images by the imaging portion 22 and the like are wired therein. The control-signal lines and the transmission-signal lines are connected with the control apparatus 3.

As shown in FIG. 2, the control apparatus 3 (medical control apparatus) has a control circuit 33. The control apparatus 3 is configured to receive the captured image by the imaging portion 22 of the endoscope 2 and transmit them as display image to the display apparatus 4. The control apparatus 3 is configured to control the treatment portion 12 of the marking device 1.

The control circuit 33 is an apparatus (computer) having hardware including a processor such as a Central Processing Unit (CPU), a memory and the like so as to be able to execute program. Functions of the control circuit 33 is realizable as the functions of the program (software) by making the control circuit 33 to read and execute the program for controlling the processor. At least part of the control circuit 33 may be configured by exclusive logic circuit and the like. Furthermore, the same functions may be realized by connecting at least part of the hardware configuring the control circuit 33 by communication lines.

Figure 5:
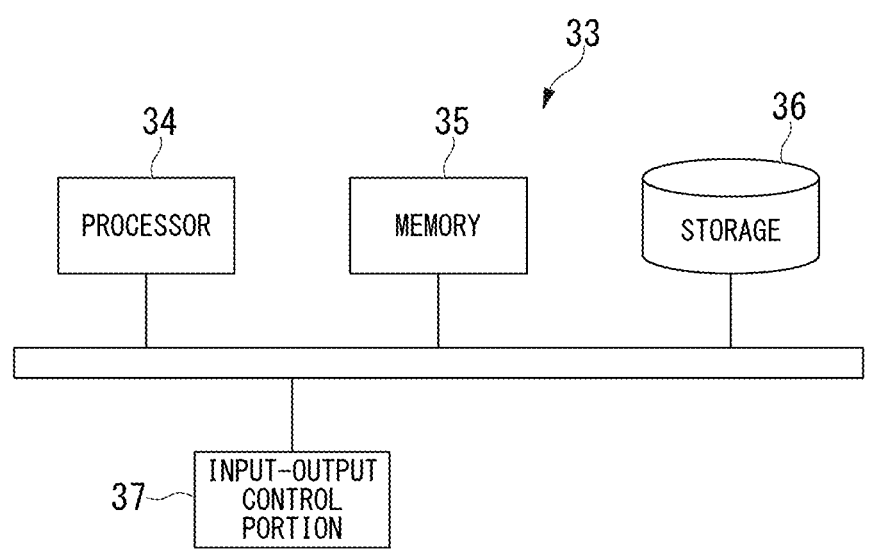
FIG. 5 is a view showing an overall configuration example of a control circuit of the control apparatus of the medical system.

FIG. 5 is a view showing an overall configuration example of the control circuit 33.

The control circuit 33 has a processor 34, a memory 35 capable of reading program, a storage 36 and an input-output control portion 37. The program supplied to the control circuit 33 for controlling the operation of the circuit 33 is read into the memory 35 and executed by the processor 34.

The storage 36 is a non-volatility recording medium for storing the above-described program and necessary data. The storage 36, for example, may be configured from a ROM or a hard disk and the like. The program stored in the storage 36 is read into the memory 35 and executed by the processor 34.

The input-output control portion 37 receives input data from the endoscope 2 and transmits the input data to the processor 34 and the like. The input-output control portion 37 is configured to generate data and control signals with respect to the marking device 1, the endoscope 2 and the display apparatus 4 according to the instructions from the processor 34.

The control circuit 33 is configured to receive the captured image as the input data from the endoscope 2 and causes the captured image to be read in the memory 35. The processor 34 performs image processing with respect to the captured image according to the program read into the memory 35. The captured image to which the image processing is performed is transmitted to the display apparatus 4 as the display image.

The control circuit 33 is configured to generate the display image by performing image processing with respect to the captured image, such as an image format transformation, a contrast adjustment, and a resize processing. The control circuit 33 performs the image processing of superimposing a virtual image of the separation line SL described below on the display image.

The control circuit 33 is configured to control the treatment portion 12 of the marking device 1. The control circuit 33 selects the application elements 15a satisfying conditions described below among the plurality of application elements 15a and controls the selected application elements 15a to apply energy. The control circuit 33 selects the light-emitting elements 16a satisfying conditions described below among the plurality of light-emitting elements 16a and controls the selected light-emitting elements 16a to emit light.

The control circuit 33 is not limited to a single apparatus having hardware. For example, the control circuit 33 may be configured by separating the processor 34, the memory 35, the storage 36 and the input-output control portion 37 as individual hardware and connecting the hardware by communication lines. Otherwise, the control circuit 33 may be configured by separating the storage 36 and implementing a cloud system by connecting the storage 36 using communication lines.

The control circuit 33 may have further configurations necessary for controlling the operations of the control apparatus 3 besides the processor 34, the memory 35, the storage 36 and the input-output control portion 37 as shown in FIG. 5. For example, the control circuit 33 may further have an image calculation portion configured to perform part or the whole of the image processing and image recognition processing by the processor 34. By further including the image calculation portion, the control circuit 33 may execute particular image processing and image recognition processing rapidly. An image transmission portion configured to perform the transmission of the display image from the memory 35 to the display apparatus 4 may be further implemented.

The display apparatus 4 is an apparatus configured to display the display image transmitted by the control apparatus 3. The display apparatus 4 has a conventional monitor 41 such as an LCD display and the like. The display apparatus 4 may have multiple monitors 41. The display apparatus 4 may have a head mounted display or a projector instead of the monitor 41.

The monitor 41 may perform a GUI display by displaying a Graphic User Interface (GUI) image generated by the control apparatus 3. For example, the monitor 41 may display the control information and caution information of the medical system 100 as the GUI display to the surgeon. In a case in which an information input from the surgeon is necessary for the control circuit 33, the control circuit 33 may control the display apparatus 4 to display a message for prompting the information input from the input apparatus 5 and other GUI display necessary for the information input.

Then input apparatus 5 is an apparatus configured to input instructions of the surgeon to the control circuit 33. As shown in FIG. 2, the input apparatus 5 has an input portion 51 and an operation input portion 52.

The input portion 51, for example, is a keyboard or a mouse. The input portion 51 may be configured by a switch or a touch panel. The touch panel may be integrally configured with the monitor 41. The input to the input portion 51 is transmitted to the control circuit 33.

The operation input portion 52 is an apparatus configured to input operation instructions with respect to the treatment portion 12 of the marking device 1. For example, the operation input portion 32 has an operation button, and the operation button is an energization-permission button for inputting the instruction of permitting the energization to the marking device 1. The input to the operation input portion 52 is transmitted to the control circuit 33. The control circuit 33 permits the energization to the treatment portion 12 according to the operation to the operation input portion 52.

[Operation of Medical System 100]

Next, operations of the medical system 100 will be described by taking the laparoscopic surgery as an example by referring to FIG. 6 to FIG. 11. According to the present embodiment, living tissues of the liver L are taken as the target tissues.

The Surgeons perform preoperative planning to create anatomical information of the target tissues using conventional method before the laparoscopic surgery. For example, the surgeons create three-dimensional shape data of the target tissues as the anatomical information from a plurality of CT images. A three-dimensional coordinate system of the three-dimensional shape data generated during the preoperative planning is referred to as a "model coordinate system (first coordinate system) C1".

The surgeons create a model M of the target tissues during the preoperative planning. The model M is associated with the three-dimensional coordinates in the model coordinate system C1, and positions of each part of the model M may be specified by the three-dimensional coordinates in the model coordinate system C1. The position coordinate (three-dimensional coordinate in the model coordinate system C1) of the tumor TU removed during the laparoscopic surgery is included in the model M.

The model M of the target tissues created as the anatomical information during the preoperative planning is stored in the storage 36 of the control circuit 33 of the control apparatus 3 (anatomical information acquisition processing). The model M may be created by an external device besides the medial system 100, or the medical system 100 may obtain the created model M from the external device.

The control apparatus 3 extracts and stores a plurality of characteristic points F in the model M (characteristic point extraction processing). The plurality of characteristic points F are extracted by using conventional characteristic point extraction method. The plurality of characteristic points F, together with characteristic values calculated according to a predetermined standard suitable to express the characteristic, are specified by the three-dimensional coordinates in the model coordinate system C1 and stored in the storage 36. The extraction and the storage of the plurality of characteristic points F may be performed before the surgery or during the surgery.

Subsequently, operations of the medical system 100 during the laparoscopic surgery will be described. The surgeon creates multiple holes (openings) for locating the trocar T in the abdomen of the patient and punctures the trocar T into the holes.

Subsequently, the scopist operates the endoscope 2 to insert the insertion portion 20 of the endoscope 2 through the trocar T puncturing the abdomen of the patient so as to introduce the insertion portion 20 into the abdominal cavity. Subsequently, the surgeon inserts the insertion portion 10 of the marking device 1 through the trocar T puncturing the abdomen of the patient so as to introduce the insertion portion 10 into the abdominal cavity. As shown in FIG. 1, the surgeon also inserts the insertion portion 10A of the assistance treatment device 1A through the trocar T so as to introduce the insertion portion 10A into the abdominal cavity. The surgeon uses the assistance treatment device 1A to hold the marking device 1.

Figure 6:
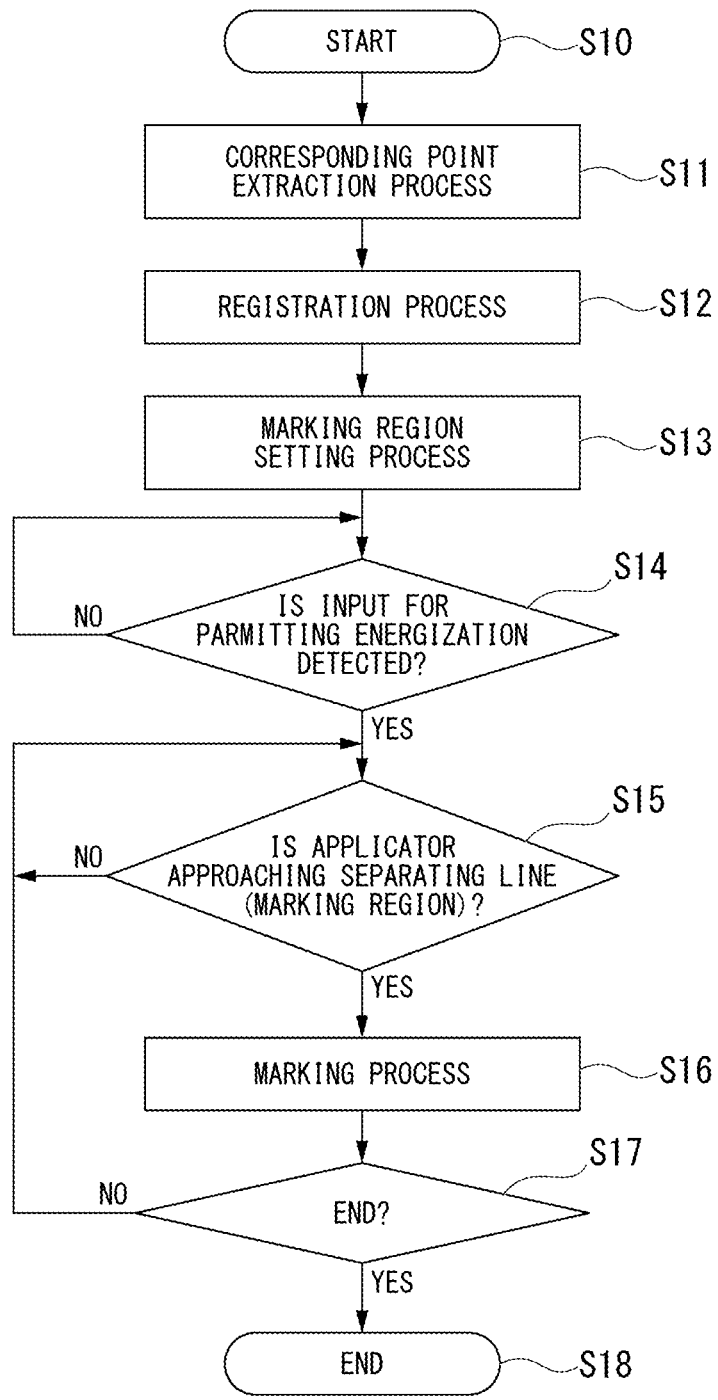
FIG. 6 is a control flow chart of the control circuit.

Hereinafter, the description will be made following the control flow chart of the control circuit 33 shown in FIG. 6. As shown in FIG. 6, when the control circuit 33 is started up, the control circuit 33 performs the initiation and starts the control (Step S10). Subsequently, the control circuit 33 executes Step S11.

During Step S11, the control circuit 33 extracts a plurality of corresponding points A in the display image in correspondence with the plurality of characteristic points F (corresponding point extraction processing). The control circuit 33 extracts the corresponding points A in the display image according to the characteristic values of the characteristic points F that are stored in the storage 36 in advance. During the extraction processing, a method suitably selected from the conventional template-matching method and the like is used. A three-dimensional coordinate system of a display space for displaying the display image is referred to as a "display coordinate system (second coordinate system) C2". The three-dimensional coordinates of the extracted corresponding points A in the display coordinate system are stored in the storage 36.

During Step S12, the control circuit 33 performs position aligning (registration) of the model coordinate system C1 of the model M and the display coordinate system C2 of the display space shown by the display image according to the plurality of characteristic points F and the plurality of corresponding points A (registration processing). During the registration, a method suitably selected from the conventional coordinate transformation methods is used. For example, the control circuit 33 performs the registration by calculating the association for transforming the coordinate position in the model coordinate system C1 to the coordinate position in the display coordinate system C2.

When the control circuit 33 finishes the registration processing, the coordinate position of the model M in the model coordinate system C1 may be transformed into the coordinate position of the display space in the display coordinate system C2. Subsequently, the control circuit 33 executes Step S13.

During Step S13, the control circuit 33 sets the separation line (marking region) SL of the target tissues according to the position of the tumor TU in the display coordinate system C2 (marking region setting processing). The position coordinates of the tumor TU included in the model M in the model coordinate system C1 are transformed into the position coordinates of the tumor TU in the display coordinate system C2.

Figure 7:
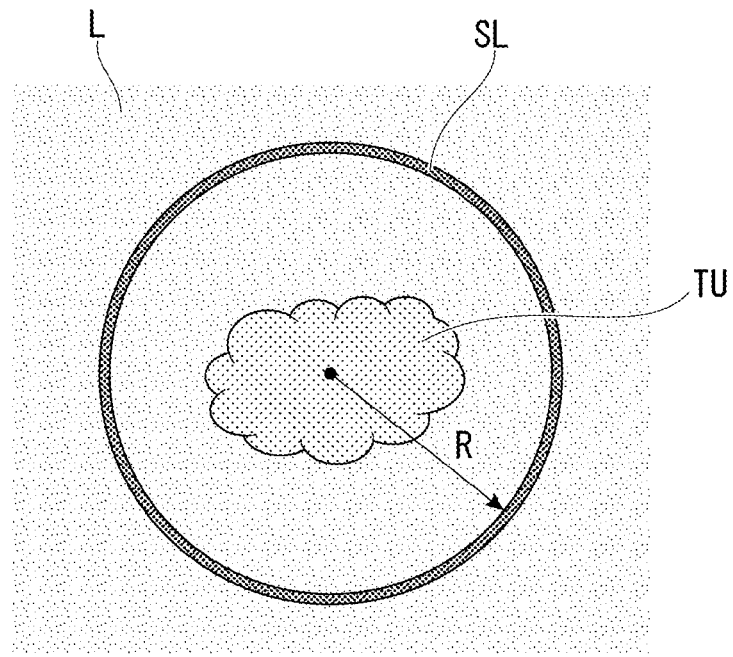
FIG. 7 is a view showing an example of a determined separation line.

FIG. 7 is a view showing an example of the determined separation line (marking region) SL.

For example, the surgeon inputs a radius R of the separation line SL from the input portion 51. The control circuit 33 sets a circle on the surface of the target tissues as the separation line SL, wherein the circle has the input radius R from the center of the tumor TU.

Figure 8:
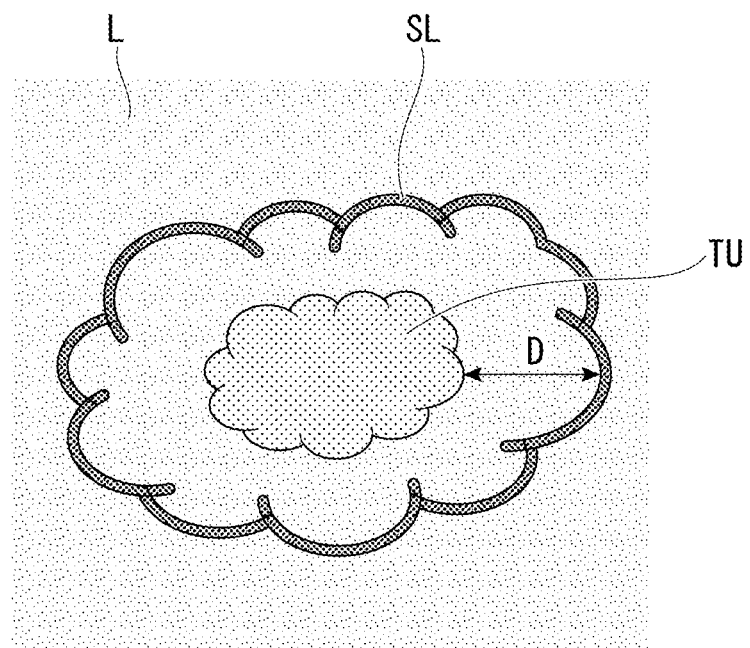
FIG. 8 is a view showing an example of the determined separation line.

FIG. 8 is a view showing an example of the determined separation line (marking region) SL.

For example, the surgeon inputs a margin distance D of the separation line SL from the input portion 51. The control circuit 33 sets a line on the surface of the target tissues as the separation line SL, wherein the line is set to around the tissue TU and has the margin distance D from the external edge of the tumor TU.

Figure 9:
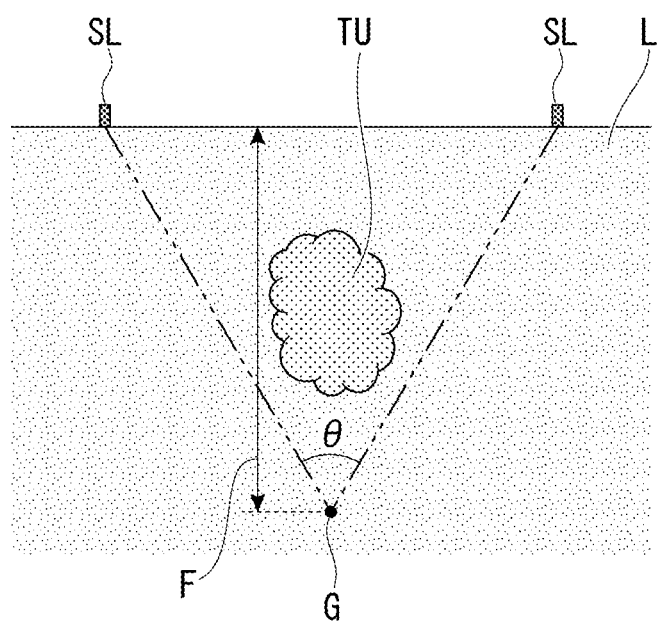
FIG. 9 is a view showing an example of the determined separation line.

FIG. 9 is a view showing an example of the determined separation line (marking region) SL.

For example, the surgeon inputs a depth F and a resection angle θ of the separation line SL from the input portion 51. A position having the depth F at the central point of the tumor TU is set to be a reference point G, and the control circuit 33 sets an intersection line of the surface of the target tissues and a cone having an apex at the reference point G and an apex angle equal to the resection angle θ as the separation line SL.

In a case in which the input portion 51 is a pen tablet, the surgeon may use the pen tablet so as to directly trace on the tablet where the display image is displayed using the pen. The control circuit 33 may set the region in the display image that is designated by the user using the pen as the separation line SL.

The control circuit 33 generates a virtual image of the determined separation line SL in the display coordinate system C2 and superimposes the virtual image on the display image. The control circuit 33 subsequently executes Step S14.

During Step S14, the control circuit 33 detects the input for permitting the energization. The control circuit 33 is on standby until the input for permitting the energization from the operation input portion 52 is detected. When the control circuit 33 detects the input for permitting the energization, the circuit 33 executes Step S15.

Figure 10:
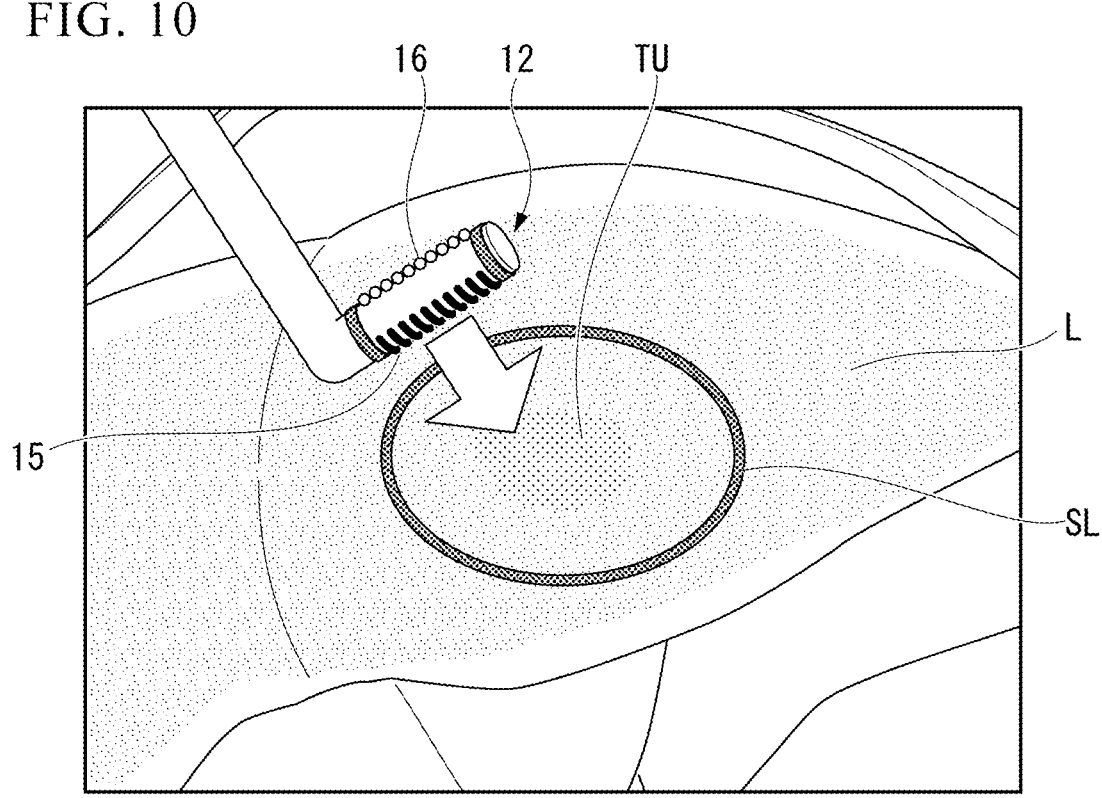
FIG. 10 is a view showing the treatment portion approaching the separation line.

FIG. 10 is a view showing the treatment portion 12 approaching the separation line SL.

After the surgeon inputs the instruction for permitting the energization to the marking device 1 from the operation input portion 52, the surgeon moves the treatment portion 12 to approach the separation line SL.

During Step S15, the control circuit 33 detects whether the applicator 15 approaches the separation line (marking region) SL according to the information indicating the separation line (marking region) SL. More specifically, the control circuit 33 detects whether at least one of the application elements 15a of the applicator 15 and the separation line approach to each other to a markable distance. The markable distance refers to a distance from which the application element 15a is capable of performing the marking on the surface of the target tissues. The application element 15a according to the present embodiment is the monopolar electrode such that the markable distance refers to the distance that the application element 15a and the target tissues come in contact with each other. A region in the separation line (marking region) SL where the applicator 15 approaches until the markable distance is defined as a "proximity area PA".

The control circuit 33 may determine an overlapping region where the superimposed separation line SL and a device region in which the applicator 15 is displayed in the display image overlap with each other as the proximity area PA.

The control circuit 33 may determine the proximity area PA by performing image processing with respect to the display image. According to the image processing, for example, the distance between the imaging portion 22 and the application element 15a and the distance between the imaging portion 22 and the surface of the target tissues shown by the separation line SL are calculated and compared. It is possible to attach a contact sensor to each application element 15a and only permit the application element 15a which is in contact with the target tissues.

The control circuit 33 may determine the proximity area PA from the three-dimensional position of the separation line SL and the applicator 15. For example, the applicator 15 has a position sensor. The control circuit 33 calculates the position coordinate of the applicator 15 in the display coordinate system C2 according to the output of the position sensor. The control circuit 33 compares the position coordinate of the separation line SL in the display coordinate system C2 and the position coordinate of the applicator 15 in the display coordinate system C2 so as to determine the proximity area PA.

The control circuit 33 is on standby until the proximity area PA is determined. When the proximity area PA is determined, the control circuit 33 executes Step S16.

Figure 11:
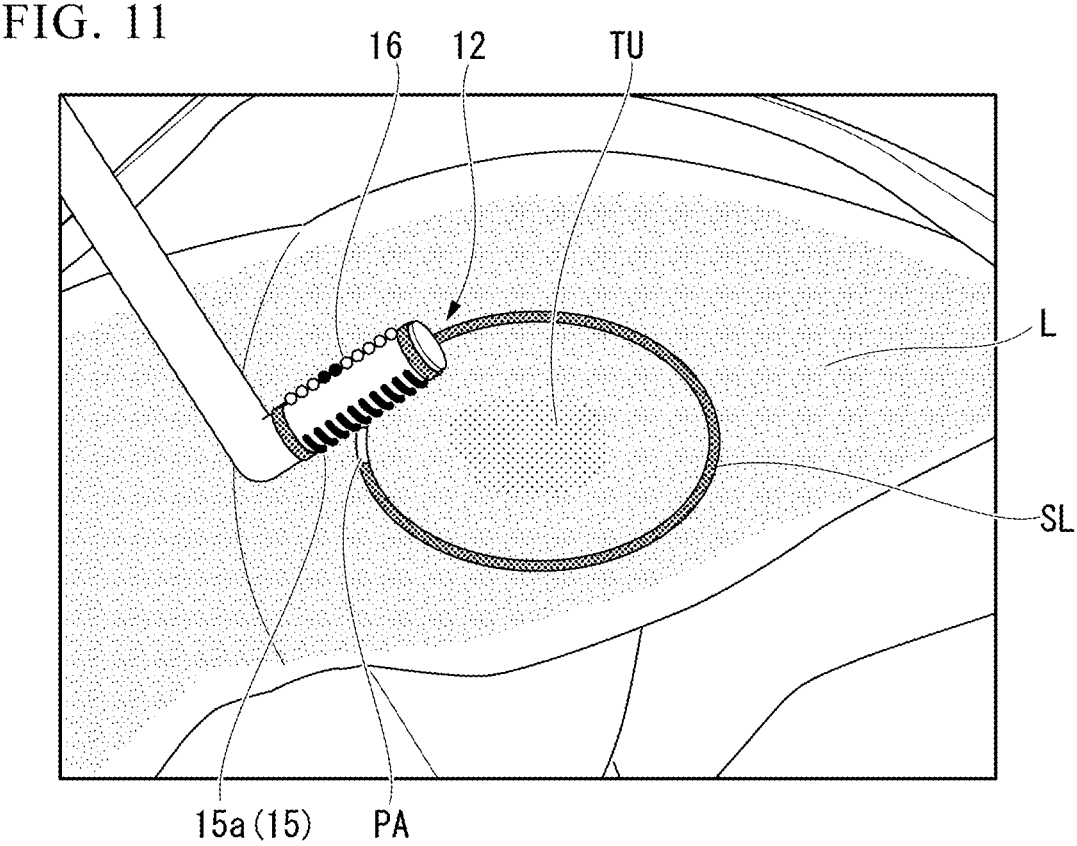
FIG. 11 is a view showing the treatment portion whose heating element is generating heat.

FIG. 11 is a view showing the treatment portion 12 whose application element 15a generates heat.

During Step S16, the control circuit 33 causes the application element 15a closest to the proximity area PA to generate heat so as to cauterize the surface of the target tissues (marking processing). In a case in which multiple application elements 15a approach the separation line SL at the markable distance, all of the corresponding application elements 15a may be controlled to generate heat. The light-emitting elements 16a emit light in response to the heat generation of the corresponding application elements 15a. The surgeon may identify the application elements 15a which are generating heat by visually confirming the positions of the light-emitting elements 16a which are emitting light.

The control circuit 33 subsequently executes Step S17. During Step S17, the control circuit 33 determines whether to finish the control processing. In a case in which the control processing is not finished, the control circuit 33 executes Step S15 again. In a case in which the control processing is finished, the control circuit 33 subsequently executes Step S18 and finished the control processing.

According to the control apparatus 3 and medical system 100 disclosed in the present embodiment, the surgeon may simply and accurately perform the marking processing along the separation line SL on the surface of the target tissues by moving the treatment portion 12 to trace on the separation line SL until the whole surface on the separation line SL is cauterized. Since the light-emitting elements 16a corresponding to the application elements 15a emit light, the surgeon may easily identify the application elements 15a which are generating heat.

The applicator 15 of the marking device 1 is disposed on the external circumferential surface of the columnar-shaped treatment portion 12. As shown in FIG. 3, the treatment portion 12 may be disposed to be orthogonal with respect to the insertion portion 10. Accordingly, the surgeon may perform the marking processing on the surface of the target tissues by sliding the treatment portion 12 inserted into the abdominal cavity on the surface of the target tissues only. The surgeon may simply and accurately perform the marking without greatly moving the treatment portion 12 in the narrow abdominal cavity.

The first embodiment of the present disclosure has been described above in details by referring to figures; however, the specific configuration is not limited to the embodiment and design changes are possible without departing from the spirit of the present disclosure. The configuration elements shown in the above-described embodiment and following modification examples may be suitably combined.

First Modification Example

For example, according to the above-described embodiment, the light emitter 16 emits light only when the applicator 15 is activated; however, the embodiment of the light emitter is not limited thereto. The light emitter may emit multicolor light. For example, the light emitter capable of emitting multicolor light may be configured to emit red color light when the applicator 15 is activated and emit blue color light when the contact sensor included in the applicator 15 detects the predetermined condition.

Second Modification Example

For example, according to the above-described embodiment, the application element 15a is the monopolar electrode; however, the embodiment of the application element is not limited thereto. The application element only has to be able to cauterize the target tissues by extracting energy, for example, the application element may be a laser light source. In the case in which the application element is the laser light source, the markable distance is larger than the markable distance according to the first embodiment.

Third Modification Example

For example, according to the above-described embodiment, the separation line (marking region) SL is formed in a linear shape; however, the embodiment of the separation line (marking region) is not limited thereto. The separation line (marking region) may have a surface shape.

Fourth Modification Example

Figure 12:
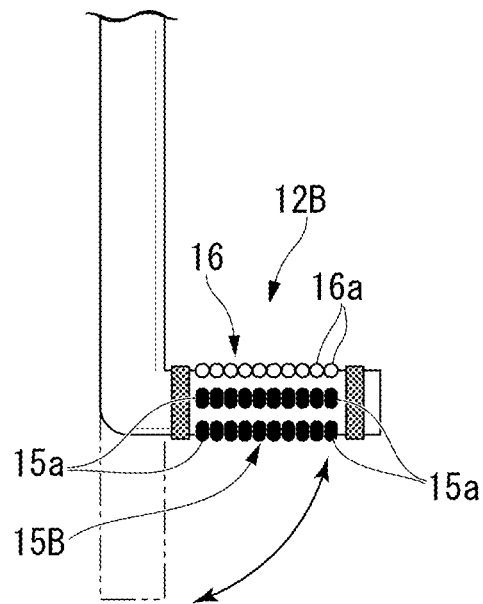
FIG. 12 is a view showing the treatment portion having a modification example of an applicator.

For example, according to the above-described embodiment, the applicator 15 is configured from the plurality of application elements 15a arrayed along the axial direction A; however, the embodiment of the applicator is not limited thereto. FIG. 12 is a view showing a treatment portion 12B having an applicator 15B as a modification example of the applicator 15. The applicator may be configured to have a plurality of application elements 15a arrayed in two rows as the applicator 15B shown in FIG. 12. The applicator may be configured to have the plurality of application elements 15a arrayed in three or more than rows.

Second Embodiment

A second embodiment of the present disclosure will be described by referring to FIG. 13. In the following description, the common configuration that has been described will be designated with the same reference sign and the duplicated description will be omitted. A control apparatus 3C (not shown) according to the present embodiment is different from the control apparatus 3 according to the first embodiment in the control processing with respect to the marking device 1C. The configuration of the control apparatus 3C is the same with that of the control apparatus 3 according to the first embodiment.

Figure 13:
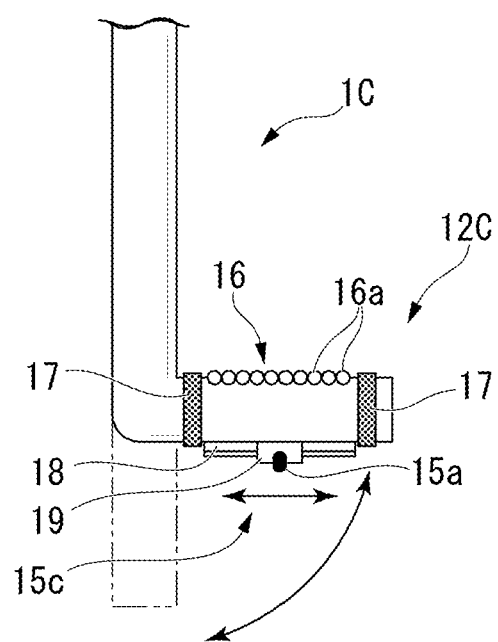
FIG. 13 is a view showing the treatment portion of the marking device that is controlled by a control apparatus according to a second embodiment of the present disclosure.

FIG. 13 is a view showing a treatment portion 12C of the marking device 1C.

The treatment portion 12C is formed in a columnar shape and rigid. The treatment portion 12C has an applicator 15C, the light emitter 16 and the marker 17. The applicator 15C and the light emitter 16 are disposed on the external circumferential surface of the treatment portion 12C and disposed to sandwich the central axis O in the axial direction A to be at opposite sides with each other.

The applicator 15C has a guide rail 18, a slider 19 and the application element 15a. The guide rail 18 is a rail extending along the axial direction A of the treatment portion 12C. The slider 19 is attached to the guide rail 18 to be advanceable and retractable. The application element 15a is attached to the slider 19. The control circuit 33 may cause the slider 19 to move along the guide rail 18 so as to move the application element 15a.

After detecting the proximity area PA, the control circuit 33 is configured to move the application element 15a to a region closest to the proximity area PA and then activate the application element 15a. Accordingly, the control circuit 33 causes the application element 15a in the proximity area PA to generate heat so as to cauterize the surface of the target tissues (marking processing).

According to the control apparatus 3C disclosed in the present embodiment, it is possible to only activate the application element 15a in the proximity area PA without arraying the plurality of application elements 15a so as to simply and accurately performing the marking processing.

The second embodiment of the present disclosure has been described above in details; however, the specific configuration is not limited to the embodiment and design changes are possible without departing from the spirit of the present disclosure. The configuration elements shown in the above-described embodiments and modification examples may be suitably combined.

Several embodiments and modification examples of the present disclosure have been described above; however, the technical scope of the present disclosure is not limited to the embodiment and the application examples. The present disclosure is not limited to the above-described embodiments and is limited only by the accompanying claims.

What is claimed is:

1. A medical control apparatus comprising:
one or more processors comprising hardware, the one or more processors being configured to:
set a marking region in each of a plurality of images showing a target tissue and a plurality of application elements;
process the plurality of images to determine whether the plurality of application elements are being moved relative to the target tissue to approach the marking region;
in response to determining that the plurality of application elements are being moved to approach the marking region, process the plurality of images to determine an overlapping region of the marking region and the plurality of application elements as a proximity area;
process the plurality of images to select a subset of the plurality of application elements shown in the plurality of images having a predetermined distance relationship with the proximity area in the plurality of images; and
selectively control the subset of the plurality of application elements to apply energy.

2. The medical control apparatus according to claim 1, wherein the one or more processors are configured to:
determine whether an applicator including the plurality of application elements approaches the proximity area; and
in response to determining that the applicator approaches the proximity area, selectively control the subset of the plurality of application elements to apply the energy.

3. The medical control apparatus according to claim 2, wherein the one or more processors are configured to:
generate the plurality of images of the target tissue according to captured images of the target tissue;
superimpose the marking region on the plurality of images of the target tissue to set the marking region in the plurality of images of the target tissue; and
determine the overlapping region of the marking region and the applicator in the plurality of images as the proximity area.

4. The medical control apparatus according to claim 2, wherein the one or more processors are configured to determine whether the applicator approaches the proximity area by image processing.

5. The medical control apparatus according to claim 1, wherein the one or more processors are configured to set the marking region based on user input.

6. The medical control apparatus according to claim 5, wherein the user input comprises a radius of a circular separation line from the center of the target tissue, and the circular separation line is the marking region.

7. The medical control apparatus according to claim 5, wherein the user input comprises a margin distance of a separation line from external edges of the target tissue, and the separation line is the marking region.

8. The medical control apparatus according to claim 5, wherein the user input comprises a depth and a resection angle associated with a cone-shaped separation line, and the cone-shaped separation line is the marking region.

9. The medical control apparatus according to claim 1, wherein the one or more processors are configured to set the marking region according to anatomical information obtained in advance.

10. A medical system comprising:
the medical control apparatus according to claim 1; and
a marking device comprising an applicator comprising the plurality of application elements.

11. The medical system according to claim 10,
wherein the marking device further comprises a plurality of light-emitting elements,
wherein the one or more processors are configured to activate a subset of the plurality of light-emitting elements to emit light, and
wherein the subset of the plurality of light-emitting elements are arranged at a corresponding position on an opposite side of the subset of the plurality of application elements controlled to apply the energy.

12. The medical system according to claim 11,
wherein the one or more processors are configured to perform image processing of an image of the subset of the plurality of light-emitting elements.

13. The medical system according to claim 11, wherein the marking device comprises:
a treatment portion including the applicator; and
an insertion portion, wherein the treatment portion is configured to be bendable relative to the insertion portion.

14. The medical system according to claim 13, wherein:
the plurality of application elements is located along a longitudinal axis of the marking device when the treatment portion is bent to be located along the longitudinal axis of the marking device; and
the plurality of light-emitting elements is located along the longitudinal axis of the marking device when the treatment portion is bent to be located along the longitudinal axis of the marking device.

15. The medical system according to claim 10,
wherein the one or more processors are configured to:
obtain three-dimensional positions of the applicator and the marking region; and
determine a region in the marking region that is a predetermined distance from the applicator as the proximity area.

16. The medical system according to claim 15, wherein the one or more processors are configured to control the subset of the plurality of application elements closest to the proximity area to apply the energy.

17. The medical system according to claim 15, wherein:
the applicator comprises a position sensor;
the three-dimensional positions of the applicator is obtained from an output of the position sensor; and
the one or more processors are configured to compare the three-dimensional positions of the marking region with the three-dimensional positions of the applicator to determine the region in the marking region is the predetermined distance from the applicator.

18. The medical system according to claim 10, wherein the marking device comprises:
a treatment portion including the applicator; and
an insertion portion, wherein the treatment portion is configured to be bendable relative to the insertion portion.

19. The marking device according to claim 18, wherein the plurality of application elements is located along a longitudinal axis of the marking device when the treatment portion is bent to be located along the longitudinal axis of the marking device.

20. The medical control apparatus according to claim 1, wherein application of the energy causes the subset of the plurality of application elements being selectively controlled to generate heat for cauterizing a surface of the target tissue.

* * * * *